United States Patent [19]
Digenis et al.

[11] Patent Number: 5,672,359
[45] Date of Patent: Sep. 30, 1997

[54] MULTICOMPARTMENT HARD CAPSULE WITH CONTROL RELEASE PROPERTIES

[75] Inventors: George A. Digenis; Dagmar Noskova, both of Lexington, Ky.

[73] Assignee: The University of Kentucky Research Foundation, Lexington, Ky.

[21] Appl. No.: 560,946

[22] Filed: Nov. 20, 1995

Related U.S. Application Data

[63] Continuation of Ser. No. 94,637, Jul. 21, 1993, abandoned.
[51] Int. Cl.⁶ ...................................................... A61K 9/52
[52] U.S. Cl. .................... 424/463; 424/452; 424/453; 424/454; 424/455; 424/456; 424/408
[58] Field of Search ........................ 424/408, 433, 424/436, 438, 417, 452, 456–463, 494, 502; 514/962, 965, 967

[56] References Cited

U.S. PATENT DOCUMENTS

| | | | |
|---|---|---|---|
| 2,451,022 | 10/1948 | Dommann | 424/408 |
| 3,122,475 | 2/1964 | Schaeppi | 167/64 |
| 3,197,369 | 7/1965 | Widmann et al. | 167/64 |
| 3,415,249 | 12/1968 | Sperti | 167/64 |
| 3,814,809 | 6/1974 | Gordon | 424/19 |
| 4,707,362 | 11/1987 | Nuwayser | 424/433 |
| 4,828,840 | 5/1989 | Sakamoto et al. | 424/470 |
| 4,880,830 | 11/1989 | Rhodes | 424/470 |
| 4,994,279 | 2/1991 | Aoki et al. | 424/494 |
| 5,023,088 | 6/1991 | Wong et al. | 424/473 |
| 5,156,849 | 10/1992 | Byrne et al. | 424/451 |
| 5,219,572 | 6/1993 | Sivarmakrishnan | 424/438 |
| 5,262,173 | 11/1993 | Sheth et al. | 424/494 |
| 5,271,945 | 12/1993 | Yoshioka et al. | 424/489 |
| 5,314,697 | 5/1994 | Kwan et al. | 424/480 |
| 5,320,853 | 6/1994 | Noda et al. | 424/472 |
| 5,472,708 | 12/1995 | Chen | 424/451 |

FOREIGN PATENT DOCUMENTS

| | | | |
|---|---|---|---|
| 0274150 | 3/1964 | Australia | 424/463 |
| 4157820 | 5/1978 | Japan . | |
| 0046826 | 4/1979 | Japan | 424/DIG. 15 |
| 0073017 | 6/1981 | Japan | 424/DIG. 15 |
| 56-73018 | 6/1981 | Japan | 424/DIG. 15 |
| 143109 | 4/1976 | United Kingdom . | |

OTHER PUBLICATIONS

Merck Index, Abstract 6101, Miconazole, p. 972.
Merck Index, Abstract 139, Acyclovir, p. 24.
Porter, S.C. "Coating of Pharmaceutical Dosage Forms", *Remington's Pharmaceutical Sciences,* 18th Ed.(1990) published by Mack Publishing Co., Easton, PA, pp.1666–1675.
Kraeling, M.E.K. and Ritschel, W.A. "Development of a Colonic Release Capsule Dosage From and the Absorption of Insulin", *Meth. Find. Exp. Clin. Pharmacol.,* vol. 14, No. 3, (1992) pp. 199–209.

*Primary Examiner*—Neil S. Levy
*Attorney, Agent, or Firm*—Lowe, Price, LeBlanc & Becker

[57] ABSTRACT

The present invention relates to a hard capsule made from a material such as gelatin, starch or a hydrophilic polymer. The capsule of the present invention is formulated into a delivery system which incorporates pharmacologically active components in three or more distinct compartments. When three compartments are utilized in the capsule, the outer compartment incorporates a drug and excipients into a layer which coats the outer part of the capsule. This layer represents the rapid release portion of the delivery system. The intermediate compartment comprises a powder formulation comprised of a drug and excipients which represents the intermediary speed release portion of the delivery system. The innermost compartment incorporates the active ingredient or ingredients in a multiparticulate form, such as small pellets, and represents the slow release component of the delivery system.

18 Claims, 4 Drawing Sheets

5,672,359

MULTICOMPARTMENT HARD CAPSULE WITH CONTROL RELEASE PROPERTIES

This application is a continuation of application Ser. No. 08/094,637 filed Jul. 21, 1993 now abandoned.

TECHNICAL FIELD

The present invention relates to a hard capsule which can deliver a desirable agent, such as a drug or an odoriferous agent, over a prolonged period of time.

The invention provides a hard capsule made from gelatin, starch or a hydrophilic polymer, such as hydroxypropyl methylcellulose (HPMC) or carboxymethyl cellulose, which by virtue of its design and composition provides an immediate and sustained mode of release of its pharmacologically active or otherwise desirable components in an aqueous environment.

BACKGROUND ART

Suppositories are known to be useful in the delivery of drugs. For example, U.S. Pat. No. 3,814,809 to Gordon et al. discloses a vaginal suppository composed of CARBO-WAX™ and a medicament such as prostaglandin.

Suppositories may be multilayered. Japanese Publication Nos. JP-150,421 and JP-150,422 disclose a multi-layered suppository. In each layer, one or more medical components are mixed with one or more water-soluble base materials such as Macrogol. The suppository disclosed in the Abstract of 150,422 contains two layers and does not contain an outer coating layer.

Japanese Application 065289 discloses a two-layered suppository comprising successively charged molten water-soluble bases (Macrogol or glycerogelatin). The suppository includes a water-soluble base layer in the lower half of the suppository and a fat-soluble base layer in the upper half. The suppositories are both rapid and long-acting. This suppository does not include an outer coating layer which includes a drug to provide immediate drug release.

Japanese Application 102,055 discloses a slow-release rectal suppository which is the product of connecting a suppository prepared with a water-soluble base material and a suppository prepared with a water-soluble base material and surface coated with a base material which is insoluble in water and which does not melt quickly at rectal temperatures. The water-soluble base material may be a mixture of gelatin and glycerine or a mixture of two or more Macrogol. The coated suppository is a slow-releasing rectal suppository and does not include an outer coating layer which includes a drug to provide immediate drug release.

UK Patent 1,431,092 discloses that certain types of suppositories have thin protective coatings, which may also contain medicaments or the like are, and which are sometimes used to reduce premature melting. This outer coating appears to teach away from the use of a fast releasing outer coating which contains a drug.

U.S. Pat. No. 3,197,369 to Widman et al. discloses coated gelatin capsules. The coating of the gelatin capsule does not contain a medicament for immediate drug release.

U.S. Pat. No. 3,122,475 to Schaeppi discloses a multilayer suppository containing sequentially acting medicaments effective for treating heart decompensation. In this suppository, the core represents about one-fifth to one-third of the total weight of the suppository and the shell represents the remaining four-fifth to two-thirds. The suppository core can be composed of cocoa butter, solidified glycerin or paraffinic wax. The suppository shell can be composed of the same ingredients and melts at 37° to 38° C.

U.S. Pat. No. 3,415,249 to Sperti discloses a suppository comprising a first and second body. The first body consists of a suppository base and a coating. The base may be a polyethylene glycol and the coating may also be a polyethylene glycol. Sperti also discloses that the base of the coating should have a substantially lower melting point than the base of the suppository. Sperti discloses that it is possible to locate a thin barrier layer over the body of the suppository prior to the application of the coating. Such an additional layer may be of moisturized gelatin. The coating can contain an anesthetic substance and the body of the suppository contains a medicament such as an agent for the stimulation of cellular respiration. The thin barrier layer does not contain a medicament.

U.S. Pat. No. 4,707,362 to Nuwayser discloses a vehicle for providing both rapid release and prolonged release of a drug. The vehicle may be a vaginal suppository. The suppository body melts at body temperature and includes a bioerodible film insert. The suppository may contain a spermicide such as Nonoxynol-9. The suppository does not include three compartments for differential drug release.

U.S. Pat. No. 4,880,830 to Rhodes discloses a slow release formulation for the preparation of tablets, capsules, suppositories or implants (see column 2, line 59) which comprises granules which are composed of particles comprising an inactive ingredient and a primary matrix of water-soluble slow release material in which are dispersed particles comprising an active ingredient. The formulation also contains a secondary matrix of water-soluble dispersible slow release material in which the granules of medicament are dispersed. At least one of the matrices may be gelatin. The suppository can contain secondary granules which are of a larger size than primary granules, and if desired tablets or capsules may be enteric film or sugar coated. Rhodes does not disclose a fast releasing outer coating containing a medicament.

U.S. Pat. No. 4,828,840 to Sakamoto et al. discloses a sustained released formulation of a water-soluble active ingredient comprising an inert core, a powder coating layer surrounding the core, a second powder coating layer surrounding the first powder coating layer, and a film coating layer surrounding the second powder coating layer. The film coating layers include polyvinylpyrrolidone, hydroxypropyl methylcellulose and starches. The film coating layer does not contain a medicament.

An example of a controlled release product which is commercially available is the product PROCARDIA XL™ distributed by Pfizer (1235 East 42nd St., New York, N.Y.). This is an extended release tablet which is designed to provide the cardiovascular drug nifedipine at an approximate constant rate over 24 hours (PDR 47th Ed. 1993, Medical Economics Data). In PROCARDIA XL™ the tablet depends for its action on the existence of an osmotic gradient between the contents of its bilayer core and the fluid in the GI tract. Drug delivery is essentially constant as long as the osmotic gradient remains constant, and then it gradually falls to zero. Upon swallowing, the biologically inert components of the tablet remain intact during GI transit and are eliminated in the feces as an insoluble shell. The osmotic gradient in this tablet is achieved by the introduction of a semipermeable membrane surrounding an osmotically active drug core. The core is divided into two layers: an "active" layer containing the drug, and a "push" layer containing pharmacologically inter (but osmotically active)

components. As water from the gastrointestinal tract enters the tablet, pressure increases in the osmotic layer and "pushes" against the drug layer, releasing the drug through a precision laser drilled tablet orifice in the active layer.

There is a need in the medical and pharmaceutical disciplines for a drug delivery system which incorporates pharmacologically active components in three or more differentially releasing drug compartments. This need particularly exists in vaginal applications wherein the release of the drug has to begin shortly after administration such as in the case of a spermicide or an anti-HIV agent and in which the drug release must continue for several hours to achieve the desired spermicidal and anti-HIV result.

The drug delivery system of the present invention provides a capsule of differentially releasing distinct compartments. The outer compartment provides a rapid release of a drug incorporated into the outer compartment. An intermediate compartment provides an intermediary speed release portion of the delivery system. And the innermost compartment provides a slow release component of the delivery system. The drug delivery system overcomes inadequacies of prior capsule formulations to provide controlled immediate and prolonged release of a desired agent in an aqueous environment.

DISCLOSURE OF THE INVENTION

The present invention provides a hard capsule drug delivery system comprising at least one inner compartment, at least one intermediate compartment surrounding the at least one inner compartment and at least one outer compartment surrounding the at least one intermediate compartment, and wherein each compartment comprises at least one drug component.

The present invention provides a drug delivery system of a hard capsule comprising an outer compartment, an intermediate compartment and an inner compartment, wherein the rate of release of the drug component of the outer compartment is faster than the rate of release of the intermediate compartment, and the rate of release of the intermediate compartment is faster than the rate of release of the inner compartment.

In a further embodiment, the invention provides a hard capsule drug delivery system comprising at least one inner compartment, at least one intermediate compartment surrounding the at least one inner compartment and at least one outer compartment surrounding the at least one intermediate compartment, and wherein each compartment comprises at least one drug component, wherein the outer compartment begins release of the drug component about 1 minute after immersion of the hard capsule into an aqueous medium and completes release of the drug component about 45 to 50 minutes after immersion of the capsule into an aqueous medium.

A still further embodiment of the invention provides a method for manufacturing a drug delivery system comprising the steps of forming a capsule comprising at least one inner compartment;

surrounding the inner compartment with at least one intermediate compartment; and surrounding the intermediate compartment with at least one outer compartment, wherein each compartment comprises at least one drug component and wherein the outer component comprises a mixture of the drug component and an excipient coating the intermediate compartment.

An additional embodiment of the invention provides complete drug or active agent release from the outer compartment of the capsule from 45 to 50 minutes after immersion of the capsule into an aqueous medium; release of the drug or active agent from the intermediate compartment occurs from 10 min. to 1.5 hours after immersion of the capsule in a liquid medium and the release of the drug from the intermediate compartment is completed from 4 to 5 hours after immersion of the capsule in a liquid medium. The initial release of the drug or active agent from an inner compartment of the drug delivery system occurs from about 1 to 2 hours after immersion of the capsule in a liquid medium and the release of the drug from an inner compartment is completed from about 7 to 8 hours after immersion of the capsule in a liquid medium.

The invention also provides a drug delivery system useful in vaginal applications wherein the release of the drug begins shortly after administration such as in the case of a spermicide or an anti-HIV agent and in which the drug release must continue for several hours to achieve the desired spermicidal and anti-HIV result.

The capsule of invention provides an ideal vehicle for colonic drug delivery of peptide drugs and an inexpensive method for drug delivery to the gastrointestinal tract.

The multicompartment coated capsule of the invention, in an additional embodiment comprises a "One a Day" single dosage control release capsule.

Other objects, features, aspects and advantages of the invention will be more apparent to those of skill in the dispensing art from the following detailed specification taken in conjunction with the drawing figures and the accompanying claims.

DESCRIPTION OF THE INVENTION

Figure 1:
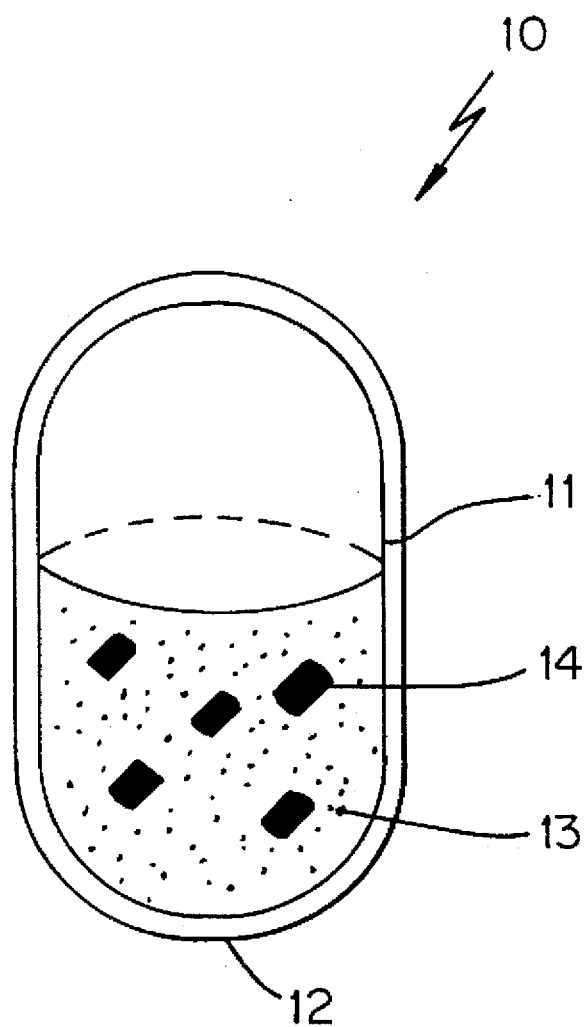
FIG. 1 shows a perspective view of the capsule of the present invention.

The present invention relates to a hard capsule formulated into a delivery system which incorporates pharmacologically active components in three or more distinct compartments.

The capsule includes at least one inner compartment, at least one intermediate compartment surrounding the at least one inner compartment and at least one outer compartment surrounding the at least one intermediate compartment, and each compartment comprises at least one drug component or active agent.

Preferably in the hard capsule the rate of release of the drug component of the outer compartment is faster than the rate of release of the intermediate compartment, and the rate of release of the intermediate compartment is faster than the rate of release of the inner compartment.

The capsule may be made from gelatin, starch, hydroxypropyl methylcellulose or carboxymethyl cellulose, for example.

When three compartments are utilized in the capsule, the outer compartment may incorporate a drug, active agent or odoriferous agent and excipients into a layer which coats and thus surrounds the intermediate component of the capsule. This outer component represents the rapid release portion of the delivery system. The intermediate compartment comprises a powder formulation which represents the intermediate rate of release portion of the delivery system. The innermost compartment incorporates the active ingredient or ingredients in a multiparticulate form, such as small pellets which may be coated or uncoated, and represents the slow release compartment of the delivery system.

Thus the drug delivery system of the invention possesses the ability to deliver a desired drug or combination of drugs from a period of time ranging from seconds after administration to several hours.

The rate of release of the drugs from a capsule consisting of three or more compartments may be controlled. An alteration in its composition as well as in the temperature will result in the changed release profile. The optimal ratio of drug to excipient in the outer compartment may be adjusted based on the drug properties and the required coating extent of the outer surface of the capsule according to methods known in the art. The release of the drug or drugs from the outer compartment of the capsule can begin as quickly as about one minute after the capsule's immersion into an aqueous medium, and a complete release of the drug in the outer compartment can occur within a period of 45 to 50 minutes after immersion.

The intermediate compartment may contain up to 300 mg of a drug powder in an 0-size capsule. Although a 0-size capsule is preferred, any size capsule may be used. Capsule size is directly related to the method of administration of the capsule. Larger capsules may be hard to swallow. If the capsule is for gastrointestinal administration 0-size, 00-size or 000-size capsules are preferred. Larger capsules may be used for vaginal or rectal administration.

Release of the drug from the intermediate or middle compartment may begin at approximately one hour after immersion of the capsule in an aqueous medium, and release may be completed within 4 to 5 hours after administration an immersion in an aqueous medium. The intermediate compartment comprises a powder drug component or active agent. The release time of the drug from this compartment could be changed by an appropriate alteration in its formulation.

The drug component or active agent contained in an inner compartment of the capsule is preferably a pellet formulation. The inner compartment consists of one or more pellets which may be coated or uncoated. The coating solution for the pellet is adapted for sustained release in the gastrointestinal tract and may contain mixtures of waxes with glycerol monostearate, stearic acid, palmitic acid, shellac and zein-polymers, ethylcellulose acrylic resins and other materials as outlined in *Remington's Pharmaceutical Sciences*. The rate of release of the drug from the inner compartment is a function of the rate of disintegration of the hard capsule wall and that of the pellets. The size of the pellet may be adjusted in accordance with the amount of drug to be delivered and the desired rate of drug release. For example, the pellets may range in size from about 1 mm to about 3 mm in diameter. The release of the drug from an inner compartment is completed from about 7 to 8 hours after immersion of the capsule in a liquid medium.

The drug delivery system is particularly useful in vaginal applications wherein the release of the drug or odoriferous agent has to begin shortly after administration such as in the case of a spermicide or an anti-HIV agent and in which the drug release must continue for several hours to achieve the desired spermicidal and anti-HIV result.

Applications of the drug delivery system include, but are not limited to the delivery of drugs for the treatment of vaginal yeast infections and for rectal use for the delivery of hemorrhoidal drugs. The capsules may contain odoriferous agents for vaginal or other delivery. The drug delivery system according to the present invention may also find internal use for controlled release delivery of drugs or vitamin nutritional supplements, or any other beneficial agent. The capsule is preferably used in the delivery of peptide drugs to the colon.

The outer compartment or coating preferably contains a drug component or active agent and an excipient component. In one embodiment of the drug delivery system the drug component or active agent and the excipient component are solubilized in alcohol, such as methanol or ethanol. Preferably the concentration of the drug component or active agent is 8% to 50% w/v. The excipient component may include CARBOWAX™ 8,000, CARBOWAX™ 4,600, CARBOWAX™3,350 or CARBOWAX™ 1,450, hydroxypropyl methylcellulose (HPMC) or mixtures thereof. CARBOWAX™ is a trademark of Union Carbide for polyethylene glycol polymers.

Additionally, when the above solid components are solubilized in water, methanol or ethanol, they form a dipping solution or spray coating, the composition of which ranges from about 10%:0%:8% to about 12.5%:10%:50% of Carbowaxes™, hydroxypropyl methylcellulose and drug, respectively. A preferred method for constructing the outer, rapid release compartment of the delivery system consists of an appropriate mixing of the desired drug with polyethylene glycol CARBOWAX™ 8,000; 4,600; 3,350; and 1,450 or a mixture of CARBOWAX™, HPMC and the drug. The hard capsule can be dipped several times or spray coated until the appropriate outer compartment is formed. This procedure may be utilized to coat hard capsules made from gelatin, starch or a hydrophilic polymer such as HPMC.

If the drug component or active agent does not include a derivative of polyvinylpyrrolidone (PVP) as an active ingredient (such as PVP-I), the excipient used in the capsule may comprise polyvinylpyrrolidone. Preferably the concentration of the excipient component is 10% to 12.5% w/v, and alternatively the concentration of the excipient is 0% to 10% w/v. When the above solid components are solubilized in water, methanol or ethanol, they form a coating solution. The composition of the coating solution preferably ranges from 10%–12.5% CARBOWAX™, from 0%–10% HPMC, and from 8%–50% drug.

According to the present invention, the drug delivery system includes an intermediate compartment comprised of a drug component or active agent and a disintegrant component. The disintegrant component may comprise from 100 mg to 180 mg of Ac-Si-Sol™, which is a modified cellulose gum which is an internally crosslinked form of a sodium salt of carboxymethyl cellulose of USP purity. The disintegrant absorbs water and swells and thus contributes to the collapse of the capsule wall, upon which the contents of the capsule are delivered. The proportion of the disintegrant to the drug determines the time of release of the capsule contents in to tie surrounding medium.

In a preferred embodiment the concentration of the drug component or active agent in the intermediate compartment ranges from about 125 to about 170 mg.

The inner compartment may also be comprised of a drug component or active agent and an excipient component. Preferably the excipient of the inner compartment is selected from lactose, magnesium stearate, Ac-Di-Sol, or calcium phosphate, or mixtures thereof. The inner compartment of the drug delivery system according to the invention includes, in a preferred embodiment, a pellet formulation comprises from 7% to 70% w/w drug component or active agent, from 10% to 84% w/w lactose, and from 6% to 20% w/w magnesium stearate. The pellets are compressed using pressure of 600–1000 pounds.

The inner compartment of the drug delivery system of the present invention is comprised of the desired drug formulated in a multiparticulate form. For example, pellets weighing 30 mg each (approximately 3 mm in diameter) can be dispersed into the inner compartment of the hard capsule. The pellets contain the drug and several excipients which determine their physical characteristics and their rate of dissolution in an aqueous medium.

Also contemplated within the scope of the present invention is a drug delivery system comprising a hard capsule with differential rates of release of the drug component or active agent as outlined below. The drug is preferably completely released from the outer compartment from 45 to 50 minutes after immersion of the capsule into an aqueous medium, the initial release of the drug from the intermediate compartment, for example, occurs from 10 min. to 1.5 hours after immersion of the capsule in a liquid medium and the release of the drug from the intermediate compartment is completed from 4 to 5 hours after immersion of the capsule in a liquid medium. The initial release of the drug from an inner compartment of the drug delivery system occurs from about 1 to 2 hours after immersion of the capsule in a liquid medium and the release of the drug from an inner compartment is completed from about 7 to 8 hours after immersion of the capsule in a liquid medium.

A preferred method for manufacturing a drug delivery system according to the invention includes the steps of forming a capsule comprising at least one inner compartment; surrounding the inner compartment with at least one intermediate compartment; and surrounding the intermediate compartment with at least one outer compartment, with each compartment comprising at least one drug component or active agent and wherein the outer component comprises a mixture of the drug component or active agent and an excipient coating the intermediate compartment.

Coating of the capsule wall which surrounds the intermediate compartment may be accomplished by dipping the capsule in the mixture of drug and excipient. Coating may also be accomplished by spray coating the capsule with the mixture of drug and excipient. Conventional dipping and coating procedures are known and acceptable for the practice of the present invention and are outlined in *Remington's Pharmaceutical Sciences*, 18th Ed. (1990) published by Mack Publishing Co., Easton, Pa., p. 1666–1675 and are incorporated herein by reference.

Drugs to be administered in the drug delivery device according to the present invention may be administered in accordance with daily dosages known in the art and as outlined in *Remington's Pharmaceutical Sciences*, 18th Ed. (1990) published by Mack Publishing Co., Easton, Pa.

Examples of drugs to be delivered vaginally include but are not limited to spermicides such as Nonoxynol-9 (nonylphenoxypolyethoxy-ethanol), Octoxynol (diisobutyl-phenoxypolyethanol), p-methanylphenyl polyoxyethylene, dodecamethylene glycol molureate, and sodium lauryl sulfate. Nonoxynol-9 is preferred. Vaginal drugs such as miconazole, acyclovir, clotrimazole, ticonizole, hormones such as estrogens; metronidazole, sulfas including sulfabenzamide, sulfacetamide, sulfacytine, sulfatrizaole; tetracycline hydrochloride, erythromycin, achromycin, chloromycetin, penicillin, chlortetracycline bacitracin, and nystatin may be administered in the drug delivery system according to the present invention. Anti-inflammatory agents such as aspirin, chlocortolone pivalate, hydrocortisone, tolmetin sodium, and indomethacin may also be administered. The drug delivery system is also useful in the delivery of germicides, such as benzalkonium and chlorhexidine and virucides, such as anti-HIV drugs.

The solubility of the drug in the coating solvent does create a limitation on the practice of the invention. The coating procedure can be practiced with a highly soluble drug as well as a completely insoluble drug component or active agent by coating the capsule with a coating suspension as set forth in example 6.

In a preferred embodiment, the capsule of the invention is used for the colonic delivery of peptide drugs. Certain peptide drugs can be delivered from the colon if they are protected from proteolytic destruction in the particular site of the gastrointestinal tract (GI).

Absorption enhancers may be used to facilitate the absorption of these relatively large peptide molecules. Consequently to achieve drug absorption of these peptides, the drug formulation preferably contains a protease (proteolytic enzyme) inhibitor and one or more absorption enhancers. See M. E. K Kraeling and W. A. Ritschel, "Development of Colonic Release Capsule Dosage Form and the Absorption of Insulin", *Meth. Find. Exp. Clin. Pharmacol.* (1992), Vol. 14(3), pp. 199–209, incorporated herein by reference.

In one embodiment the multicompartment capsule of the present invention permits the release of the absorption enhancer(s) and the protease inhibitor prior to the release of the peptide drug. This offers the advantage that the membrane of the colon is predisposed to permit the crossing of the peptide drug and thus the colon would be free of proteolytic activity at the time the drug is released from the capsule.

In this embodiment, the protease inhibitor and the absorption enhancers could either be present in the outer compartment or the outer and intermediate compartments of the multicompartment capsule. The peptide drug may be introduced in the intermediate compartment and the inner slow releasing compartment of the capsule. Alternately, the peptide drug may be introduced in only the pelletized inner compartment of the multicompartment capsule.

To achieve colonic delivery of the capsule contents, the capsules are coated with such polymer coatings as Eudragit NE 30, Eudragit S100, cellulose acetate phthalate (CAP), cellulose acetate succinate (CAS), cellulose acetate trimellitate (CAT) or cellulose acetate butyrate (CAB). The above polymers are acid resistant and dissipate from the surface of the capsule via pH-dependent and time controlled release mechanisms known in the art.

Examples of peptide drugs which may be used in the capsule of the present invention include insulin, calcitonin, interferon, interleukins and proteins in oral vaccines. Examples of absorption enhancers are fatty acids, bile salts such as sodium taurocholate, caprylate myristate, glycerides, such as phosphatidyl choline, lecitins, salicylates and lauryl sulfate. Examples of protease inhibitors for use in this embodiment of the invention, include but are not limited to bestatin, leupeptin, chymostatin, pepstatin A, papain and aprotinin.

In a further advantageous embodiment of the invention, the multicompartment capsule can be used in the design of oral drug delivery dosage forms generally referred to as "one a day" formulations. These formulations are particularly useful in drug delivery to the elderly.

Compliance in dosage regimen is often difficult to achieve, particularly among the elderly. It is therefore desirable, in the case of several drugs, to take one pill or dosage form per day ("one a day"). To achieve this regimen the dosage form has to be a delivery system that can continuously deliver the drug in a controlled release manner.

The delivery of the drug from the multicompartment capsule of the invention, in a preferred embodiment, is continuous when the drug is appropriately distributed in each of the capsule compartments. The capsule of the invention is much easier to produce and thus more cost effective than the commercially available PROCARDIA XL™ tablet. In addition, the multicompartment capsule dissipates completely prior to its elimination from the body of a patient while the PROCARDIA XL™ tablet is eliminated in the feces intact, as an insoluble shell. This insoluble tablet has the potential to provide complications to some patients.

Odoriferous agents which may be administered in the capsule according to the invention, include but are not limited to aromatic substances, fragrances, and absorbents. Examples of fragrances which may be included in the capsule are linalol and geraniol and etherial oils such as lemon oil and lavender oil. In a preferred embodiment, the capsule contains 10% citronella oil in admixture with olive oil, as a fragrance extender and enhancer.

In addition to the foregoing critical components, various optional ingredients as a conventionally used in the art, may be employed. These optional ingredients include, for example, flavorings, colorings, sweeteners, fragrances, diluents, fillers, preservatives, antioxidants, stabilizers, and lubricants.

In an alternative embodiment, the drug delivery system of the invention can be fabricated into any convenient shape for insertion into a body cavity or for administration via the gastrointestinal tract to meet a wide variety of functional requirements. Shaping can be affected, for example, by injection molding, compression molding, hot dipping, extrusion, melt casting and similar techniques.

Reference will now be made in detail to the figures including preferred embodiments and methods of the present invention.

FIG. 1 illustrates a hard capsule 10 which is formed from gelatin, starch or hydrophilic polymer, and which comprises a three compartment delivery system for its pharmacologically active components. The outer compartment 12 incorporates a drug and excipients into a layer which coats the outer part of the capsule. This outer compartment represents the rapid release portion of the capsule. The intermediate compartment 11 contains a powder formulation 13 which is introduced into the hard capsule 10 and provides an intermediate-speed release portion of the capsule. The inner compartment of the capsule contains active ingredients which are in the form of small pellets 14 and which release their drug component or active agent more slowly than that of the outer or intermediate compartments.

Figure 2:
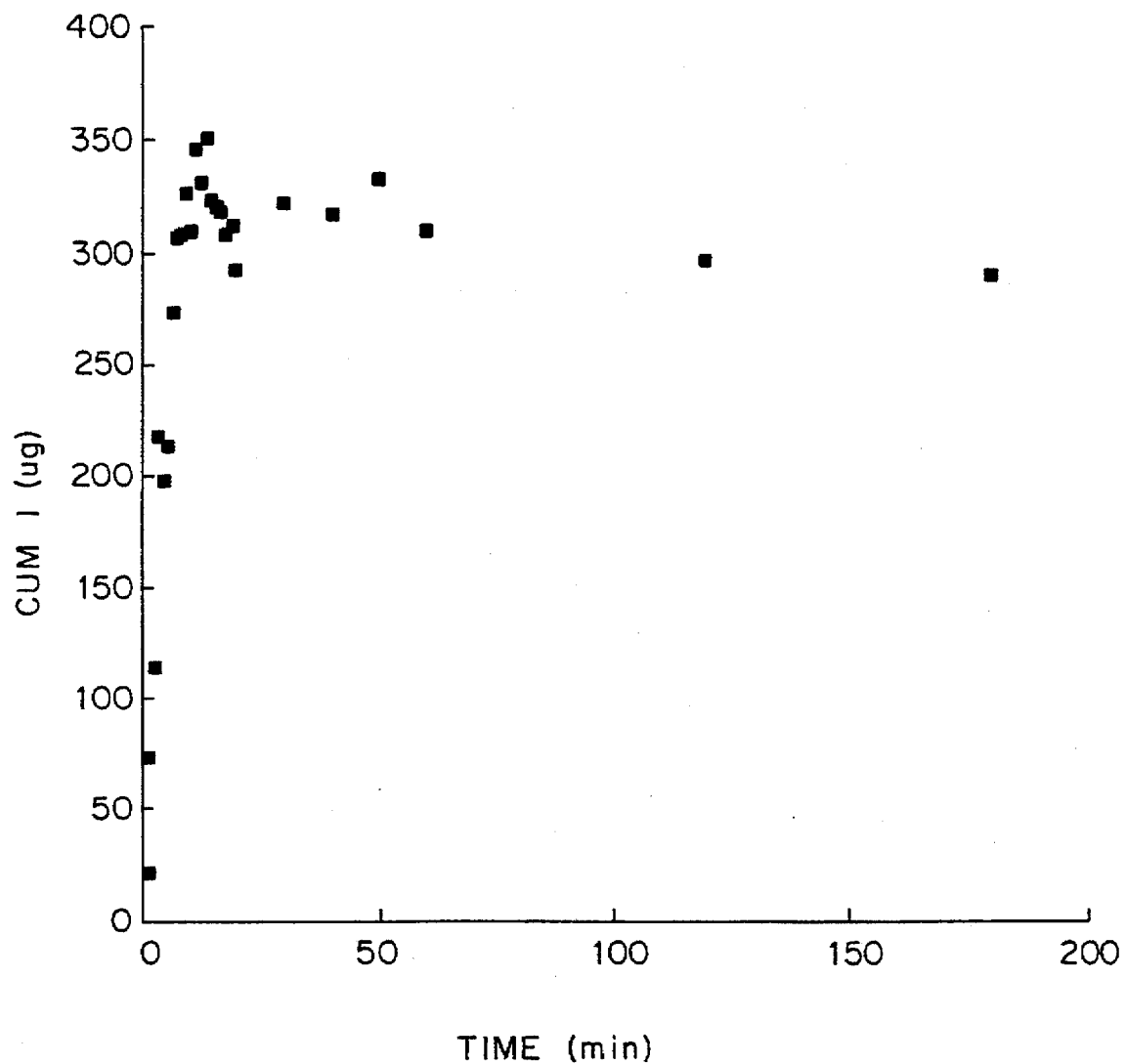
FIG. 2 shows a chart indicating the rate of release of an active component measured by the rate of iodine release from the outer compartment of the capsule.

FIG. 2 illustrates the profile of the rate of release of PVP-I/N-9, which possesses spermicidal and anti-HIV properties at pH 5.0, from the outer compartment determined spectrophotometrically measuring the release of iodine into the medium. In the embodiment illustrated by FIG. 2, a hard gelatin capsule with an outer layer of an active component and an excipient was placed into 10 mL of water at pH 5.0 and stirred at 24° C.

As can be seen from FIG. 2, the release of the active ingredients, as measured by the rate of release of iodine, from the outer compartment of the capsule begins at approximately one minute after immersion into an aqueous medium. Complete release of the PVP-I/N-9 from the outer compartment of the capsule is attained within 45–50 minutes after immersion of the capsule into the aqueous medium.

Figure 3:
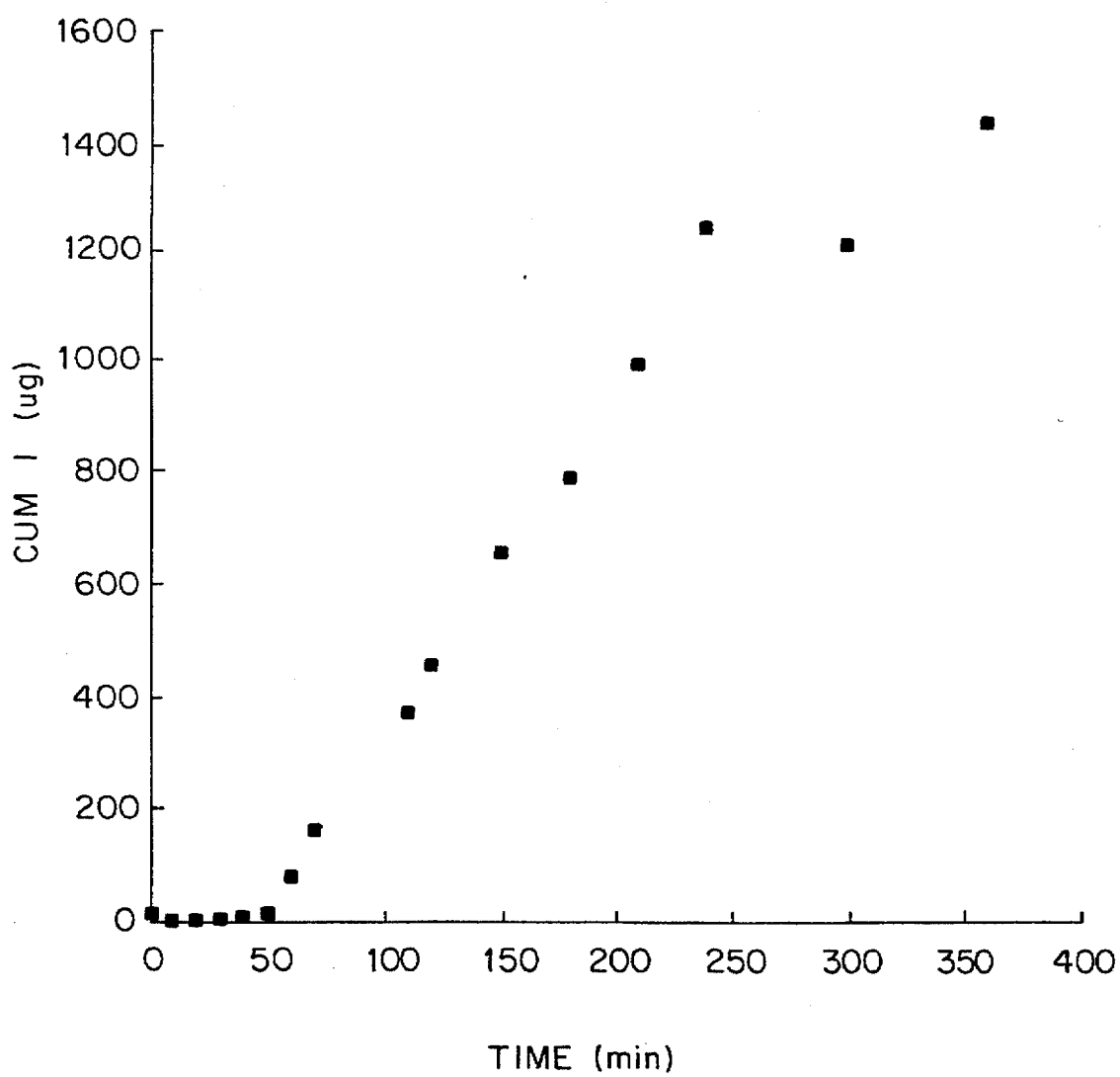
FIG. 3 shows a chart indicating the rate of release from the middle compartment of a hard capsule packed with 170 mg of PVP-I/N-9 and 170 mg of Ac-Di-Sol.

FIG. 3 illustrates the profile of the rate of release of PVP-I/N-9 from the middle or intermediate compartment, determined by spectrophotometrically measuring the release of iodine into the medium, into water at pH 5.0 stirred at 24° C. In the embodiment illustrated by FIG. 3, the rate of release of drug from the intermediate compartment of the capsule is slower than the rate of release of drug from the outer compartment as illustrated in FIG. 2.

FIG. 3 further illustrates that the release of the drug from the intermediate compartment begins approximately one hour after immersion of the capsule into the aqueous medium, and attains a complete release within 4 to 5 hours.

Figure 4:
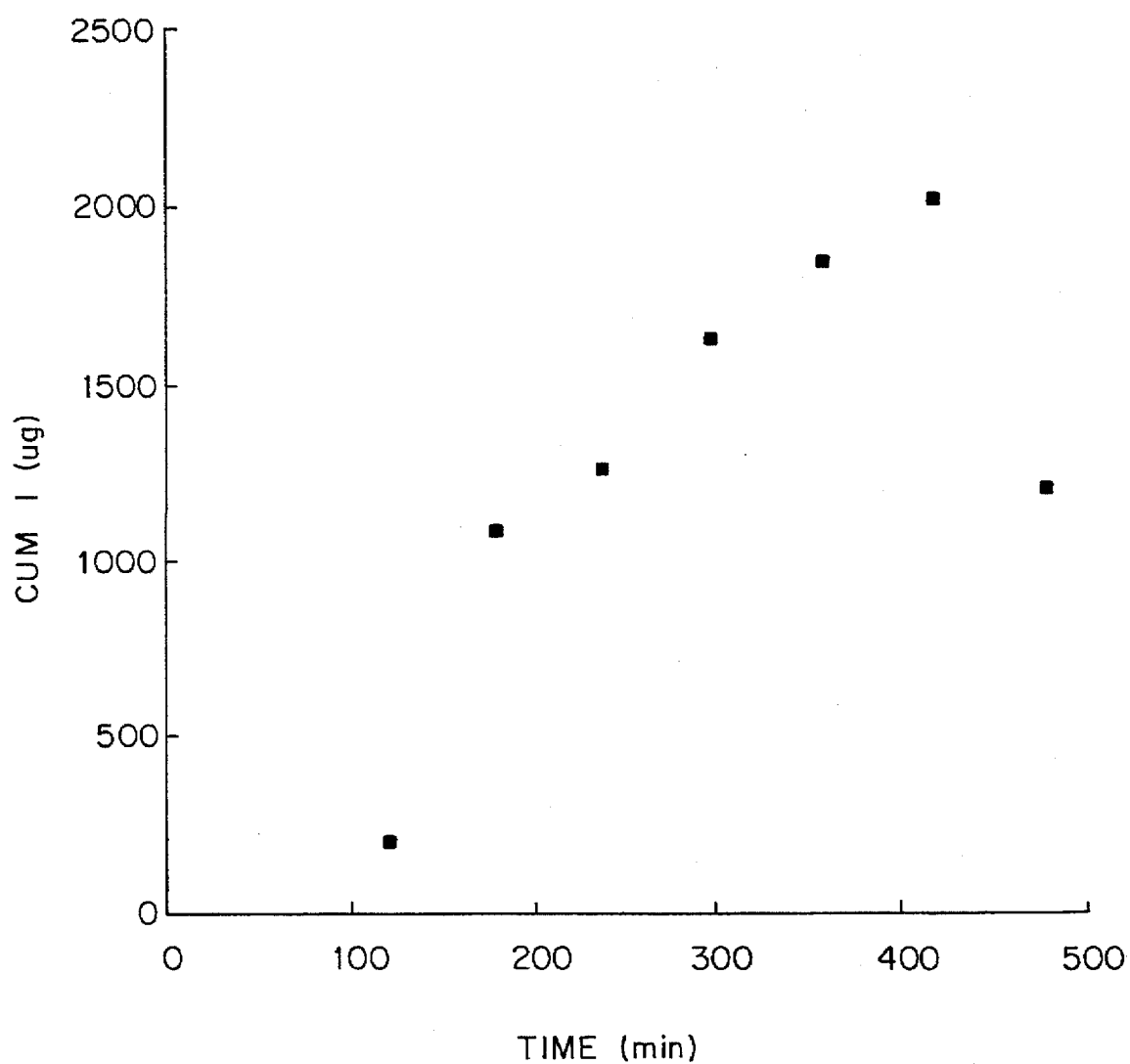
FIG. 4 shows a chart indicating the rate of release from the inner compartment of a hard capsule packed with five PCP-I/N-9 pellets dispersed into a powder containing 170 mg of PVP and 170 mg of AC-DI-SOL. The term AC-TI-SOL used throughout the specification means crosscarmellose sodium. "W/W" means "weight %" as used throughout the specification.

FIG. 4 illustrates the profile of the release of the drug PVP-I/N-9 from the inner compartment, measured spectrophotometrically by following the release of iodine into the medium, in this case water with a pH of about 5.0. In the example illustrated by FIG. 4, a hard size-0 capsule was packed with about 170 mg of PVP, 170 mg of Ac-Di-Sol and five pellets, each pellet being compressed under 600 to 1000 pounds of pressure from the mixture of 70% PVP-I/N-9, 15% calcium phosphate or lactose, 15% magnesium stearate and 0% Ac-Di-Sol. As can be seen from FIG. 4, the rate of release of PVP-I/N-9 from the inner compartment is slower than the rate of release from the intermediate compartment, as illustrated in FIG. 3, and the rate of release from the outer compartment, as illustrated by FIG. 2.

While not intending to limit the scope of the invention in any manner, the following examples are given to illustrate various potential embodiments of the present invention.

EXAMPLE 1

The various coating solutions form the creation of the outer compartment are made according to the following general procedure: Stock solutions of 30%–50% w/v of CARBOWAX™ 8,000, 4,600, 3,350, or 1,450, 0%–30% w/v hydroxypropyl methylcellulose (HPMC) and 24%–66.7% w/v are made in water or alcohol.

The appropriate amount of CARBOWAX™ stock solution is mixed with aliquots of HPMC and PVP-I/N-9 stock solutions in order to obtain the coating solution composition which ranges from 10% to 12.5% w/v of CARBOWAX, 0% to 10% w/v of HPMC and 8% to 50% w/v of PVP-I/N-9.

Subsequently, the hard gelatin capsule, size 0, is repeatedly coated by the coating solution depending upon the amount of solution desired for the outer compartment and dried until a sufficient outer compartment is formed. The extent of coating of the outer layer on a 0-size hard gelatin capsule ranges from about 10 to 80 mg. The amount of the drug in this outer compartment ranges from about 3 to 64 mg.

EXAMPLE 2

A coating solution containing the anti-HIV drug, 3-azido-3-deoxythymidine (AZT) as the active component is made according to the general procedure described in Example 1;

1 mL of 50% w/v stock solution of CARBOWAX™ 1,450 is mixed with 3 mL of 20% w/v stock solution of AZT, producing the solution of CARBOWAX™ 1,450 and AZT in a 12.5%/26.7% w/v ratio. The hard gelatin or starch capsule, size 0, is coated by the coating solution and then dried. The extent of the coating of the outer compartment on a 0-sized starch capsule ranges from about 20 to 30 mg. The amount of AZT in this outer layer ranges from about 12 to 18 mg.

EXAMPLE 3

A coating solution was made from a coprecipitate of nonoxynol-9, polyvinyl pyrrolidone and iodine (PVP-I/N-9), spermicidal with anti-HIV properties, and CARBOWAX™ 1,450 in the ratio of 50%/12% w/v. The solution successfully coated a 0-size gelatin or starch capsule. The extent of coating of the outer surface of a 0-size gelatin or starch capsule by the above described method ranged from 10 to 80 mg. This amount of coating includes the active component, in this case PVP-I/N-9, and the excipient, such as CARBOWAX™. The amount of the drug in the outer layer ranged from 3 to 64 mg. The optimal ratio of drug to excipients in the coating solution may be adjusted according to the properties of the drug and the required extent of coating in the outer layer of the capsule.

EXAMPLE 4

A coating suspension containing the antifungal drug miconazole nitrate, 1-[2,4-Dichloro-B-(2,4-dichlorobenzyl)oxy]-phenethyl-imidazole mononitrate (MONISTAT) as the active component is made according to the following procedure: 1.01 g. of miconazole nitrate is suspended in 2 mL of 50% w/v solution of PVP (polyvinylpyrrolidone) in MeOH producing the coating suspension of PVP and miconazole in a 1:1 ratio. The hard gelation or starch capsule, size 0, is coated by the coating suspension and then dried. The extent of the loading of the outer layer on a 0-size hard capsule ranges from 110 to 216 mg. The amount of miconazole nitrate in this outer layer ranges from 50 to 100 mg.

This example illustrates the solubility of the drug in the coating solvent does not create a limitation on the practice of the invention. The coating procedure can be practiced with a highly soluble drug as well as a completely insoluble drug component or active agent.

EXAMPLE 5

Solute (active component) release from the rapidly releasing compartment of the outer layer is conducted under following conditions: the hard gelatin capsule with the outer layer of the active component and excipient is placed into 10 mL (this volume is used in order to achieve similar release environment for the vaginal application) of water pH 5.0 and stirred at 24° C. or 37° C. Concentration of solute (PVP-I/N-9) in the dissolution (release) medium is followed by monitoring absorbance of iodine at 353 nm. Absorbance is converted to concentration using absorptivity of iodine determined from the calibration measurement. FIG. 2 represents an example of PVP-I/N-9 release measured by the rate of iodine release from the outer layer of the capsule.

EXAMPLE 6

Solute release from an intermediary compartment, represented by the powder formulation of the drug and excipients inside the capsule, is conducted under the following conditions: A hard capsule size-0, is filled with PVP-I/N-9 (125 mg–170 mg) and disintegrant AC-DI-SOL (100–180 mg). A hard capsule which is packed with a mixture of PVP-I/N-9 and AC-DI-SOL, is placed into 10 mL of water pH 5.0 and stirred at 24° C. to 37° C. Concentration of solute (active component PVP-I/N-9) in the release medium was followed by monitoring the absorbance of iodine at 353 nm. Absorbance is converted to concentration using absorptivity of iodine determined from the calibration measurement. FIG. 3 is an example of PVP-I/N-9 release from a hard capsule size 0, packed with 170 mg of PVP-I/N-9 and 170 mg of Ac-Di-Sol.

EXAMPLE 7

Solute release from the slow release inner compartment, represented by a multiparticulate form of PVP-I/N-9 and other excipients is conducted under the following conditions: A hard capsule size 0 is packed with filler polyvinylpyrrolidone (PVP) 170 mg, disintegrant Ac-Di-Sol 170 mg and 5 pellets (3 mm diameter, 30 mg each) are dispersed into the powder content of the hard capsule. The pellets are compressed from the mixture of PVP-I/N-9 7%–70%, calcium phosphate or lactose 84–10%, magnesium stearate 6%–20%, Ac-Di-Sol™ 3%–0, using pressure of 600–1000 pounds.

A hard capsule packed with filler, disintegrant and five pellets is placed into 10 mL of water pH 5.0 and stirred at 24° C. or 37° C. Concentration of solute (active component PVP-I/N-9) in the release medium is followed by monitoring absorbance of iodine at 353 nm. Absorbance is converted to concentration as described in Example 3. FIG. 4 is an example of PVP-I/N-9 release from the slow compartment of a hard gelatin capsule comprised from 5 PVP-I/N-9 pellets, dispersed into a powder containing 170 mg of PVP and 170 mg of Ac-Di-Sol.

EXAMPLE 8

An example of intermediate compartment delivery is set forth below. A 0-size hard gelatin capsule was filled with 125 mg of PVP-I/Nonoxynol-9 powder and 100 mg. of an internally crosslinked sodium carboxymethyl-cellulose disintegrant, USP purity, AC-DI-SOL. In this embodiment, the time of first release of the drug into water with a pH of 5.0 at 24° C. was 2 to 3 hours.

EXAMPLE 9

An example of inner compartment delivery is set forth below. A 0-size hard capsule is packed with 170 mg of a PVP filler and 170 mg of AC-DI-SOL™ and five pellets each containing 10%–84% calcium phosphate, 6%–20% magnesium stearate, 0%–3% AC-DI-SOL, and 7%–70% of the desired drug, the time of first release of the drug into water of pH 5.0 at 24° C. was within a range of 1 to 2 hours. A complete release of the drug may be attained within 7 to 8 hours.

EXAMPLE 10

Same as example 9, except that the five pellets are coated with a coating solution to prolong the time prior of drug delivery from the pellets. This coating solution adopted for sustained release in the gastrointestinal tract may contain mixtures of waxes with glycerol monostearate, stearic acid, palmitic acid, shellac and zein-polymers, ethylcellulose acrylic resins and other materials apparent to those of skill in the art as outlined in *Remington's Pharmaceutical Sciences*.

EXAMPLE 11

An example of a complete three compartment capsule is set forth below. A 0-size hard capsule is packed with 170 mg of a PVP filler and 170 mg of AC-DI-SOL™ and five 3 mm pellets, each containing 10%–84% calcium phosphate, 6%–20% magnesium stearate, 0%–3% AC-DI-SOL, and 7%–70% of acyclovir. The intermediary compartment, represented by the powder formulation of acyclovir and excipients is introduced inside the hard capsule surrounding the pellet formulation. The intermediate compartment consists of acyclovir powder (125 mg–170 mg) and disintegrant AC-DI-SOL™ (100–180 mg).

A coating solution containing acyclovir as the active component is made according to the general procedure described in Example 1; 1 mL of 50% w/v stock solution of CARBOWAX™ 1,450 is mixed with 3 mL of 20% w/v stock solution of acyclovir, producing the solution of CARBOWAX™ 1,450 and acyclovir in a 10%/15% w/v ratio. The hard gelatin or starch capsule, size 0, is coated by the coating solution and then dried. The coating solution surrounds the capsule wall and thus surrounds the intermediate drug powder compartment. The extent of the coating of the outer compartment on a 0-sized starch capsule ranges from about 20 to 30 mg. The amount of acyclovir in this outer layer ranges from about 12 to 18 mg.

EXAMPLE 12

Same as example 11, except that the instead of acyclovir the capsule contains an odoriferous agent.

EXAMPLE 13

Same as example 11, except that the instead of acyclovir the capsule contains Octoxynol, a spermicidal agent. The drug delivery system hard capsule is for vaginal delivery.

EXAMPLE 14

Same as example 11, except that the instead of acyclovir the capsule contains penicillin, an antibiotic. The drug delivery system hard capsule is for gastrointestinal delivery.

EXAMPLE 15

Peptide Capsule

A zero size hard capsule is packed with 180 mg. of taurocholate, 180 mg of sodium myristate, and 0.5 mg of leupeptine, and 10 IU of insulin. As the inner compartment of the capsule, the capsule contains three pellets, each containing 10–84% of calcium phosphate, 60–20% of magnesium stearate, and insulin 40 IU.

The outer compartment consists of two layers. The first layer contains 20 mg. of sodium taurocholate, 20 mg. of sodium myristate, 0.5 mg. of leupeptine and 3.5 mg of CARBOWAX 1450. After the first layer is established, the second layer is created by dipping (or spraying) the capsule in an aqueous dispersion of Eudragit S100 and Eudragit NE 30D in a 3:7 ratio.

EXAMPLE 16

Same as example 15, except that a 0 size hard capsule is packed with 180 mg of sodium taurocholate, 180 mg of sodium caprylate, 0.5 mg of aprotinin, calcitonin. As the inner compartment of the capsule, the capsule contains three pellets, each containing 10–84% of calcium phosphate, 60–20% of magnesium stearate, and calcitonin.

The outer compartment consists of two layers. The first layer contains 20 mg of sodium caprylate, 20 mg of sodium taurocholate, 0.5 mg of aprotinin and 3.5 mg of CARBOWAX 1450.

After the first layer is established, the second layer is created by dipping (or spraying) the capsule in an aqueous dispersion of Eudragit NE30 and Eudragit S100 30D in a 7:3 ratio. The capsule is coated with a 10% cellulose acetate phthalate in acetone/methanol (1:1 ratio) solution.

EXAMPLE 17

One a Day Capsule

A zero size hard capsule is packed with 10 mg of nifedipine, 200 mg of lactose, 100 mg of starch and 3 pellets. Each of the pellets of the inner compartment contains 10 mg–20 mg of nifedipine, 10–84% of calcium phosphate, 60–20% of magnesium stearate.

The pellets are coated with a coating solution containing glyceryl monostearate 11% w/w, glyceryl distearate 16% w/w, white wax USP 3% w/w, carbon tetrachloride 65% w/w, PVP 2%, starch 2,8% titanium oxide 0.1%, CARBOWAX 1400 0.1%.

The outer compartment is represented by 10–20 mg of nifedipine 6–13 mg of CARBOWAX and 12–26 mg of HPMC or HPC.

EXAMPLE 18

Same as Example 17, except that instead of HPMC the outer compartment contains PVP.

The purpose of the above description and examples is to illustrate some embodiments of the present invention without implying any limitation. It will be apparent to those of skill in the art that various modifications and variations may be made in the capsule and method of the present invention without departing from the spirit or scope of the invention.

We claim:

1. A hard capsule drug delivery system comprising:
   a. at least one slow rate releasing compartment comprising pellets or granules and at least one drug;
   b. at least one intermediate rate releasing compartment, said intermediate releasing compartment comprising powder or granules containing at least one drug;
   c. a hard capsule which houses said intermediate rate releasing and said slow rate releasing compartments; and
   d. a fast rate releasing outer layer comprising at least one drug and excipients, which surrounds completely said hard capsule.

2. A hard capsule according to claim 1 wherein said fast rate releasing layer releases said drug within about one minute after immersion of said hard capsule into an aqueous medium and the release is completed in about 40 to 50 minutes.

3. A hard capsule according to claim 1 wherein the release of said drug from said intermediate rate releasing compartment occurs from about 10 minutes to about 1.5 hours after immersion of said hard capsule into an aqueous medium and is completed in about 4 to 5 hours.

4. A hard capsule according to claim 1 wherein the release of said drug from said slow rate releasing compartment occurs from about 1 to 2 hours after immersion of said hard capsule into an aqueous medium and is completed in about 7 to 8 hours.

5. A hard capsule according to claim 1 wherein said hard capsule delivery system comprises a controlled release formulation for a single dosage per day delivery.

6. A hard capsule delivery system according to claim 1 wherein said delivery system is administered orally.

7. A hard capsule delivery system according to claim 1 wherein said delivery system is administered vaginally.

8. A hard capsule according to claim 1 wherein said drug in said outer fast rate releasing layer is a protease inhibitor and said drug in said intermediate rate releasing and said slow rate releasing compartments is a peptide drug.

9. A hard capsule according to claim 1 wherein said drug in said outer fast rate releasing layer and said intermediate rate releasing compartment is a protease inhibitor and said drug in said slow rate releasing compartment is a peptide drug.

10. A hard capsule of claims 8 and 9 wherein said slow rate releasing compartment further comprises an absorption enhancer.

11. A hard capsule according to claim 1 wherein said drug in said outer fast rate releasing layer and said intermediate rate and slow rate releasing compartments is nonoxynol-9.

12. A hard capsule according to claim 1 wherein said drug in said outer fast rate releasing layer and said intermediate rate and slow rate releasing compartments is an anti-HIV drug.

13. A hard capsule according to claim 1 wherein said drug in said outer fast rate releasing layer and said intermediate rate and slow rate releasing compartments is nifedipine.

14. A hard capsule according to claim 1 wherein said drug in said outer fast rate releasing layer and said intermediate rate and slow rate releasing compartments is an antimicrobial drug.

15. A hard capsule according to claim 1 wherein said outer fast rate releasing layer further comprises components selected from the group consisting of excipients, binders, plasticizers and mixtures thereof in concentration of 10–12.5% by weight of said outer fast releasing layer.

16. A hard capsule according to claim 15 wherein drug concentration in said outer fast rate releasing layer ranges from 8 to 50% by weight of said outer fast rate releasing layer.

17. A hard capsule according to claim 1 wherein said intermediate rate releasing and said slow rate releasing compartments further comprise components selected from the group consisting of excipients, binders, plasticizers and mixtures thereof in concentration of 30 to 50% by weight of said intermediate rate releasing and said slow rate releasing compartments.

18. A hard capsule according to claim 17 wherein said drug concentration in said intermediate rate releasing and said slow rate releasing compartments ranges from 50 to 70% by weight of said intermediate rate releasing and said slow rate releasing compartments.

* * * * *